(12) United States Patent
Hong

(10) Patent No.: US 7,987,612 B2
(45) Date of Patent: Aug. 2, 2011

(54) HEIGHT MEASURING DEVICE

(76) Inventor: Chuan Hong, Shanghai (CN)

( * ) Notice: Subject to any disclaimer, the term of this patent is extended or adjusted under 35 U.S.C. 154(b) by 0 days.

(21) Appl. No.: 12/964,714

(22) Filed: Dec. 9, 2010

(65) Prior Publication Data

US 2011/0072677 A1 Mar. 31, 2011

(30) Foreign Application Priority Data

Jun. 13, 2008 (CN) ...................... 2008 2 0060590 U

(51) Int. Cl.
*G01B 3/20* (2006.01)
*A61B 5/107* (2006.01)

(52) U.S. Cl. ............................................ 33/832; 33/512

(58) Field of Classification Search ............ 33/512, 33/783, 832, 833; 600/587
See application file for complete search history.

(56) References Cited

U.S. PATENT DOCUMENTS

| | | | | | |
|---|---|---|---|---|---|
| 1,996,553 | A | * | 4/1935 | Scully | 33/512 |
| 2,215,884 | A | * | 9/1940 | Runge | 33/512 |
| 2,381,428 | A | * | 8/1945 | Attick | 33/512 |
| 3,137,943 | A | * | 6/1964 | Mechaneck | 33/833 |
| 4,711,033 | A | * | 12/1987 | Mitchell | 33/833 |
| 5,402,585 | A | * | 4/1995 | Lund | 33/832 |
| 6,073,359 | A | * | 6/2000 | Lee | 33/832 |
| 6,226,881 | B1 | * | 5/2001 | Landauer | 33/512 |
| 6,519,868 | B1 | * | 2/2003 | Pryor et al. | 33/832 |
| 6,919,517 | B2 | * | 7/2005 | Montagnino et al. | 33/512 |
| 7,181,861 | B1 | * | 2/2007 | Leser | 33/832 |
| 7,891,106 | B2 | * | 2/2011 | Dunham | 33/512 |
| 2005/0155246 | A1 | * | 7/2005 | Montagnino | 33/832 |
| 2010/0223799 | A1 | * | 9/2010 | Dunham | 33/512 |
| 2010/0229412 | A1 | * | 9/2010 | Kenney | 33/512 |

* cited by examiner

*Primary Examiner* — G. Bradley Bennett
(74) *Attorney, Agent, or Firm* — Matthias Scholl P.C.; Matthias Scholl

(57) ABSTRACT

A height measuring device, including a scale, including graduation and a measuring part, and a positioning plate, the graduation and the measuring part are disposed on a right side of the scale, the measuring part is capable of moving along the graduation and indicating height, a measuring plate is disposed on the measuring part, and capable of folding as being perpendicular to or parallel to the scale, a top edge of the scale is capable of being buckled with a bottom edge of the positioning plate, a bottom edge of the scale is capable of being buckled with a top edge of the positioning plate, and a fixing part is disposed at the back of each of the scale and the positioning plate, and capable of being disposed in a vertical plane.

11 Claims, 12 Drawing Sheets

HEIGHT MEASURING DEVICE

CROSS-REFERENCE TO RELATED APPLICATIONS

This application is a continuation of International Patent Application No. PCT/CN2009/000581 with an international filing date of May 26, 2009, designating the United States, now pending, and further claims priority benefits to Chinese Patent Application No. 200820060590.7 filed on Jun. 13, 2008. The contents of all of the aforementioned applications, including any intervening amendments thereto, are incorporated herein by reference.

BACKGROUND OF THE INVENTION

1. Field of the Invention

The invention relates to a height measuring device.

2. Description of the Related Art

Nowadays, height measuring devices are widely used. However, there are several problems with conventional height measuring devices: firstly, measurement methods thereof are troublesome, and measurement results are inaccurate; secondly, they take up space in homes, and are unpractical for families with limited living area; and finally, they are not convenient for use.

SUMMARY OF THE INVENTION

In view of the above-described problem, it is one objective of the invention to provide a height measuring device that features accurate measurement and convenient use, and takes up small space.

To achieve the above objectives, in accordance with one embodiment of the invention, provided is a height measuring device, comprising a scale, comprising graduation and a measuring part, and a positioning plate, the graduation and the measuring part are disposed on a right side of the scale, the measuring part is capable of moving along the graduation and indicating height, a measuring plate is disposed on the measuring part, and capable of folding as being perpendicular to or parallel to the scale, a top edge of the scale is capable of being buckled with a bottom edge of the positioning plate, a bottom edge of the scale is capable of being buckled with a top edge of the positioning plate, and a fixing part is disposed at the back of each of the scale and the positioning plate, and capable of being disposed in a vertical plane.

In a class of this embodiment, a pair of buckling parts is disposed on a right side of the positioning plate, and the back of the scale, and capable of being buckled with each other.

In a class of this embodiment, the scale is divided into multiple sections, and a folding mechanism is disposed between two adjacent sections whereby facilitating folding of the sections.

In a class of this embodiment, the scale is divided into multiple sections, and the sections are connected to each other in a manner of inserting.

In a class of this embodiment, a pair of arc-shaped concave parts is disposed on both sides of the center of the positioning plate.

In a class of this embodiment, an upper part and a lower part of the positioning plate are axially symmetric to each other.

In accordance with another embodiment of the invention, provided is a height measuring device, comprising a scale, comprising graduation and a measuring part, and a positioning plate, the graduation and the measuring part are disposed on a right side of the scale, the measuring part is capable of moving along the graduation and indicating height, a measuring plate is disposed on the measuring part, and capable of folding as being perpendicular to or parallel to the scale, a pair of buckling parts is disposed on a right side of the positioning plate, and the back of the scale, and capable of being buckled with each other, a bottom edge of the scale is capable of being buckled with a top edge of the positioning plate, and a fixing part is disposed at the back of each of the scale and the positioning plate, and capable of being disposed in a vertical plane.

In a class of this embodiment, the scale is divided into multiple sections, and a folding mechanism is disposed between two adjacent sections whereby facilitating folding of the sections.

In a class of this embodiment, the scale is divided into multiple sections, and the sections are connected to each other in a manner of inserting.

In a class of this embodiment, a pair of arc-shaped concave parts is disposed on both sides of the center of the positioning plate.

In a class of this embodiment, an upper part and a lower part of the positioning plate are axially symmetric to each other.

Advantages of the invention comprise: the invention is simple in structure, which makes it convenient for transportation and installation, and takes small indoor space during use, and measurement results produced thereby are very accurate.

BRIEF DESCRIPTION OF THE DRAWINGS

Detailed description of the invention will be given below in conjunction with accompanying drawings.

Figure 1:
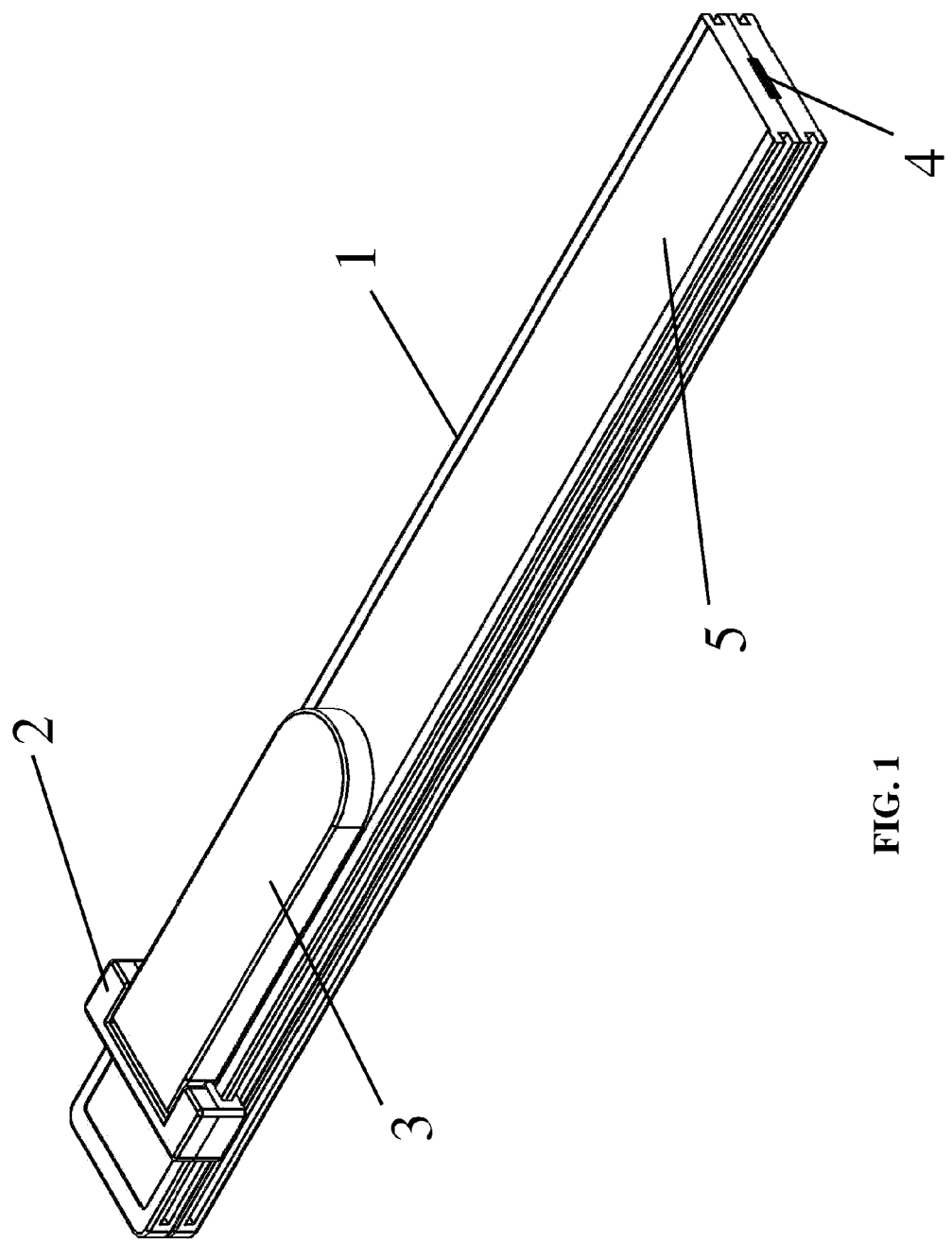
FIG. 1 is a schematic view of a scale and a measuring part of the invention.

In the drawings, the following reference numbers are used: 1—scale; 2—measuring part; 3—measuring plate; 4—leaflet; 5—right side of scale; 6—positioning plate; 7—right side of positioning plate; 8—top edge of positioning plate; 9—bottom edge of positioning plate; 10—buckling part; 11—arc-shaped concave part; 12—back of scale; 13—fixing part; 14—top edge of scale; 15—bottom edge of scale; 16—back of positioning plate.

DETAILED DESCRIPTION OF THE EMBODIMENTS

As shown in FIGS. 1-4, a height measuring device of the invention comprises a scale 1, comprising graduation and a measuring part 2, and a positioning plate 6. The graduation and the measuring part 2 are disposed on a right side 5 of the scale, and the measuring part 2 is capable of moving along the graduation and indicating height.

A measuring plate 3 is disposed on the measuring part 2, and capable of folding as being perpendicular to or parallel to the scale 1.

A top edge 14 of the scale is capable of being buckled with a bottom edge 9 of the positioning plate, and a bottom edge 15 of the scale is capable of being buckled with a top edge 8 of the positioning plate.

A fixing part 13 is disposed at the backs 12 and 16 of each of the scale and the positioning plate 6, and capable of being disposed in a vertical plane. In this embodiment, the vertical plane is wall.

A pair of buckling parts 10 is disposed on a right side of the positioning plate 7, and the back 12 of the scale, and capable of being buckled with each other.

The scale 1 is divided into multiple sections, and a folding mechanism is disposed between two adjacent sections whereby facilitating folding of the sections. Alternatively, the sections are connected to each other in a manner of inserting.

Another folding mechanism is disposed at the center of the scale 1. In this embodiment, the folding mechanism is a leaflet 4. An upper part and a lower part of the scale 1 are capable of being folded via the folding mechanism, and the back 12 of the scale is folded inwards. As shown in FIG. 1, this greatly reduces a length the scale 1, and ensures that a measurement range thereof is not to be reduced for the purpose of transportation and storage.

Figure 2:
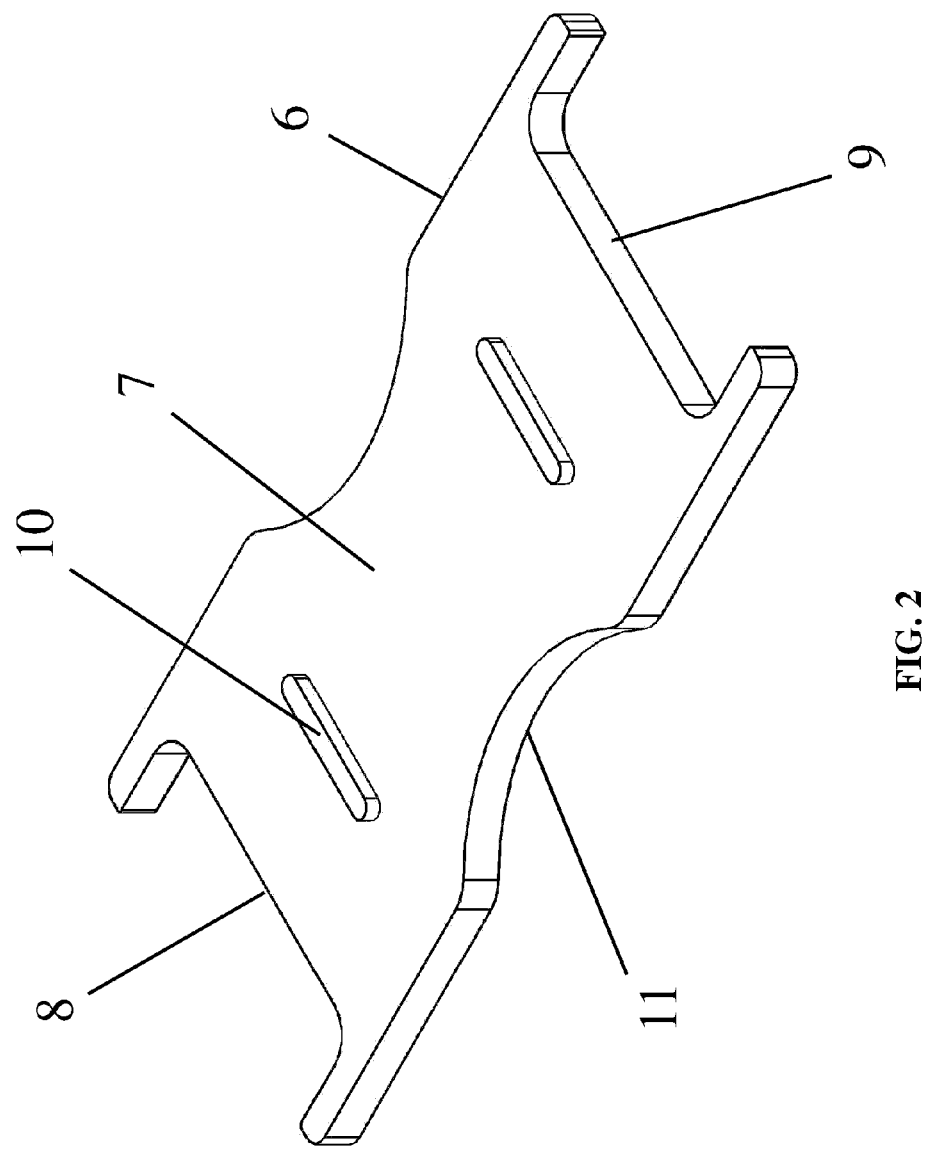
FIG. 2 is a schematic view of a positioning plate of the invention.
Figure 3:
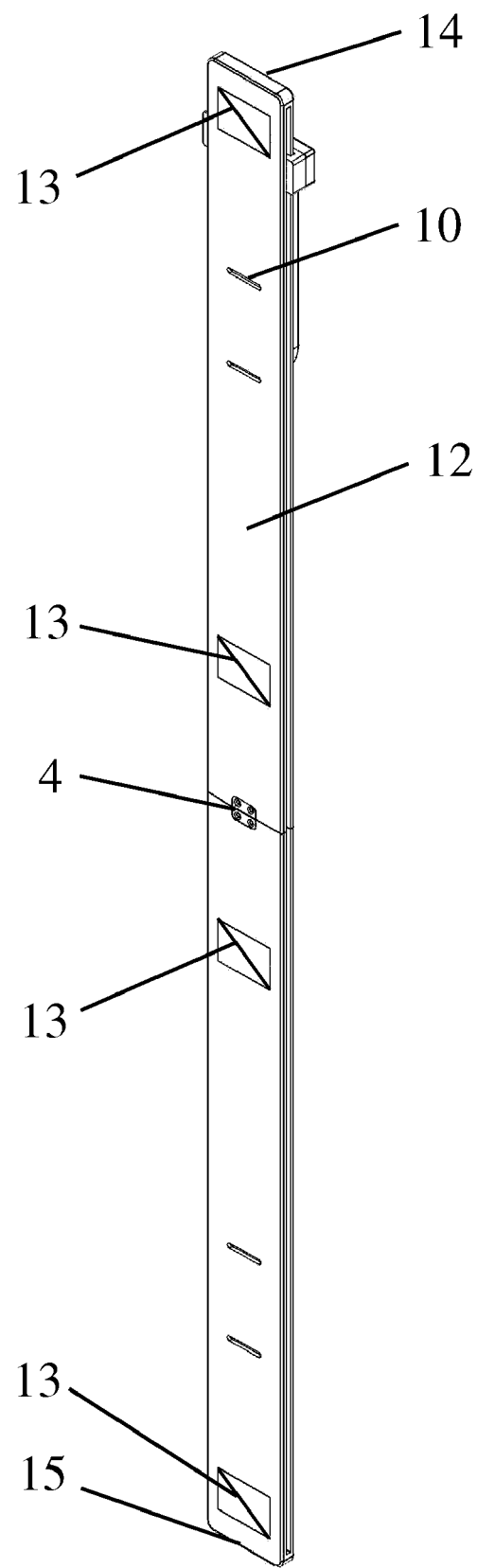
FIG. 3 is a schematic view of a back of a scale after being unfolded.
Figure 4:
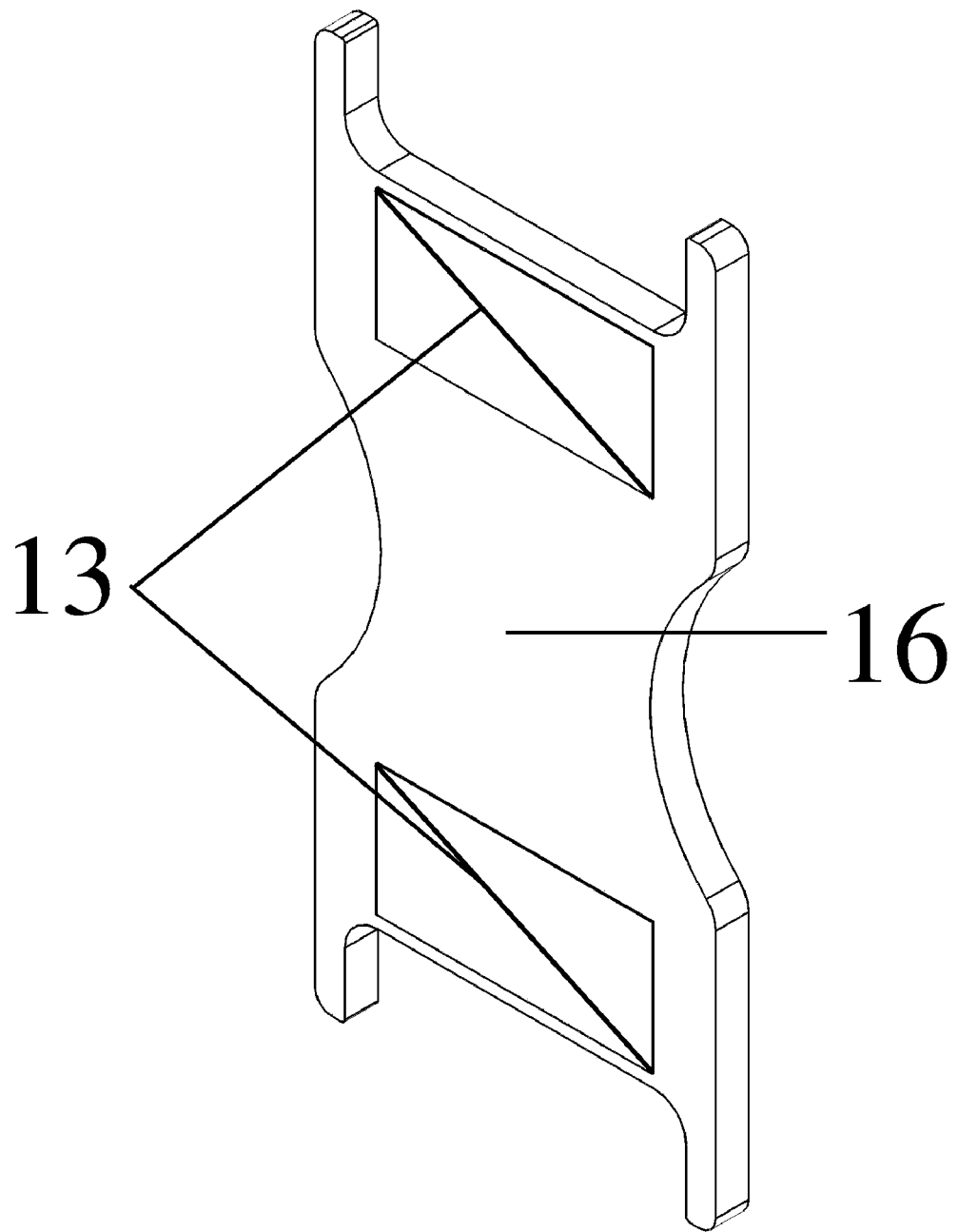
FIG. 4 is a schematic view of a back of a positioning plate of the invention.

As shown in FIG. 2, a pair of arc-shaped concave parts 11 is disposed on both sides of the center of the positioning plate 6. During installation, a user clamps the concave part 11 via his fingers, which makes the invention easy for use.

An upper part and a lower part of the positioning plate 6 are axially symmetric to each other.

As shown in FIGS. 5-8, a first method of using the height measuring device of the invention is illustrated.

Figure 5:
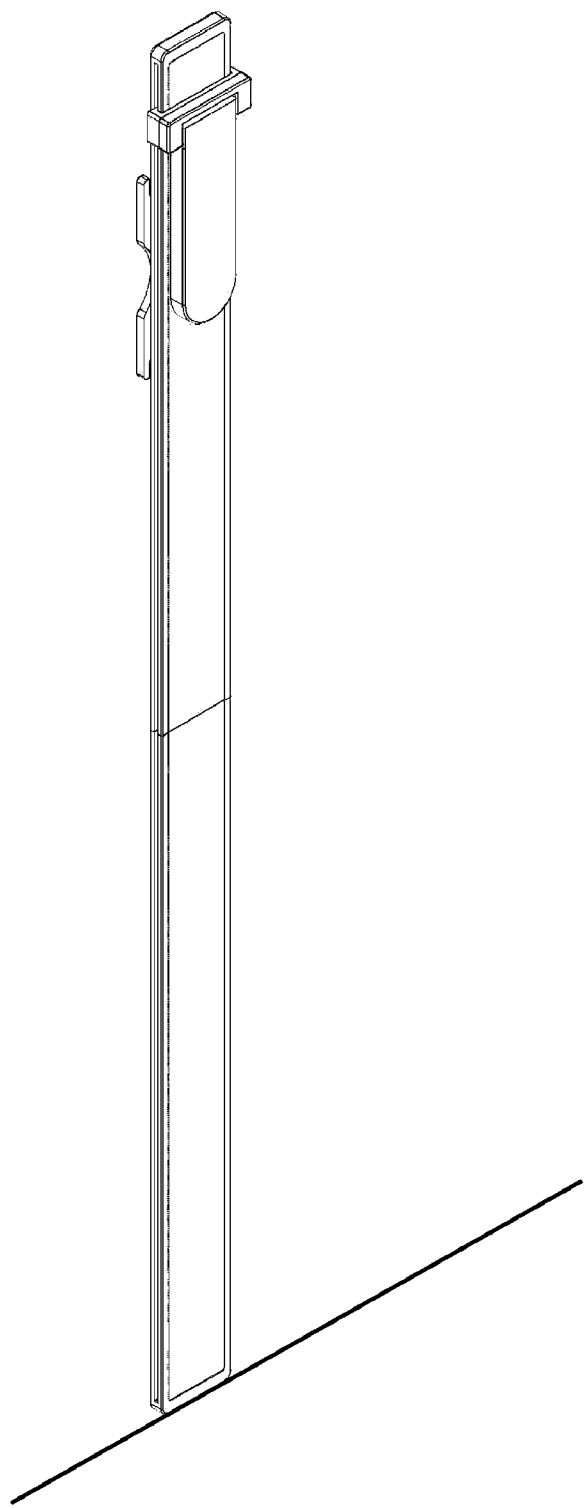
FIGS. 5-8 illustrate a method of using a height measuring device of the invention.

As shown in FIG. 5, firstly the positioning plate 6 is disposed at the back 12 of the scale via the buckling part 10, and the bottom of the scale 1 abuts against the ground, and tightly leans against the wall in a direction perpendicular to the ground. Then, the positioning plate 6 is fixed on the wall via the fixing part 13 at the back of the positioning plate 6, and the scale 1 is separated from the positioning plate 6. In this embodiment, the fixing parts 13 disposed at the back of the scale 1 and the positioning plate 6 use a gumming, a sucker, or a screw to fix the scale 1 or the positioning plate 6 on the wall. After that, the bottom edge 15 of the scale is buckled with the top edge 8 of the positioning plate, and the fixing part 13 at the back 12 of the scale fixes the scale 1 on the wall.

Figure 6:
Figure 7:
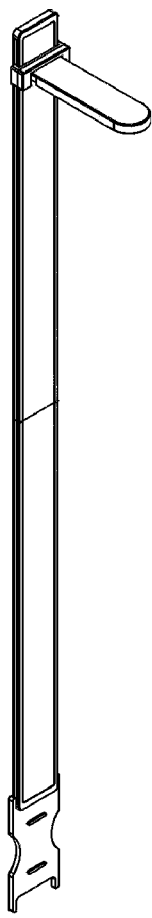
Figure 8:
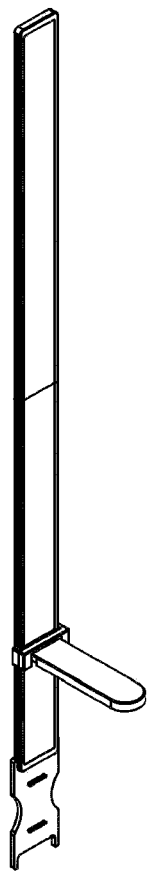

As shown in FIG. 6, after the scale 1 is fixed on the wall, it is possible to fold the measuring plate so that it is perpendicular to the scale 1, and thus height measurement of children is implemented (as shown in FIGS. 7 and 8).

As shown in FIGS. 9-12, a second method of using the height measuring device of the invention is illustrated.

Figure 9:
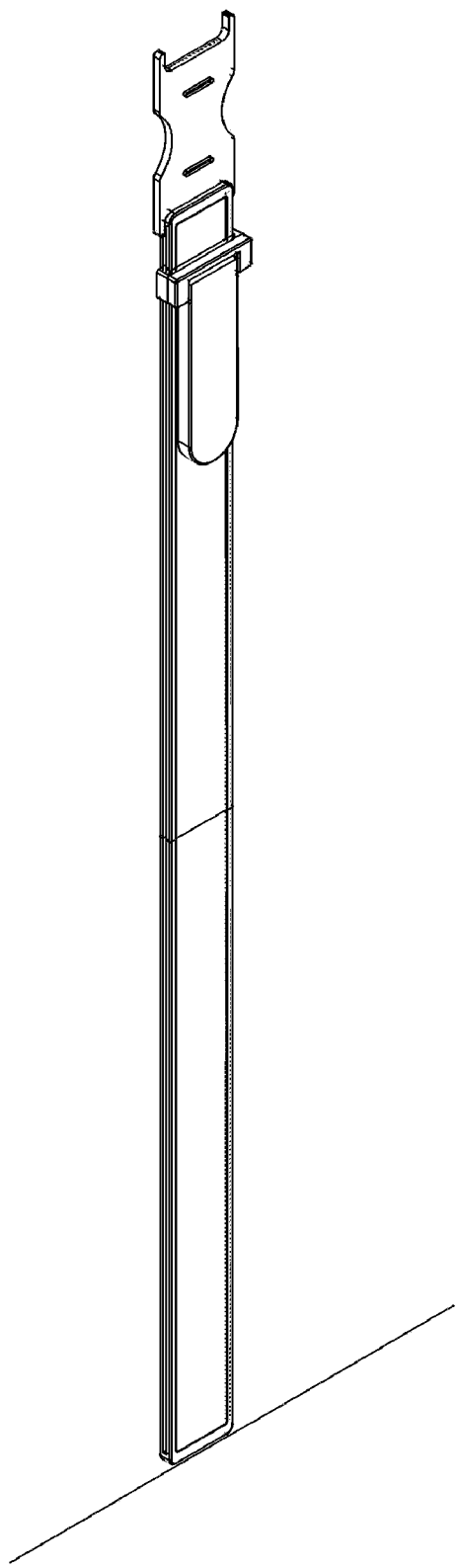
FIGS. 9-12 illustrate another method of using a height measuring device of the invention.

As shown in FIG. 9, the bottom of the scale 1 abuts against the ground, and tightly leans against the wall in a direction perpendicular to the ground. Meanwhile, the bottom edge 9 of the positioning plate is buckled with the top edge 14 of the scale. Then the fixing part 13 at the back of the positioning plate 6 fixes the positioning plate 6 on the wall.

After that, the bottom edge 15 of the scale is buckled with the top edge 8 of the positioning plate, and the fixing part 13 at the back 12 of the scale fixes the scale 1 on the wall.

Figure 10:
Figure 11:
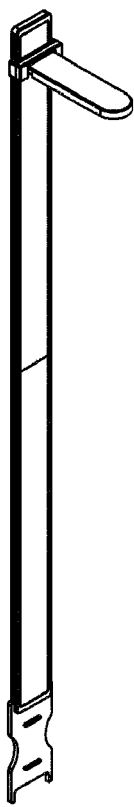
Figure 11:
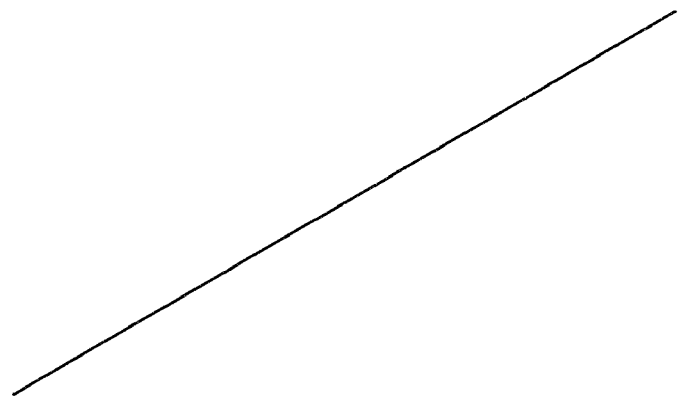
Figure 12:
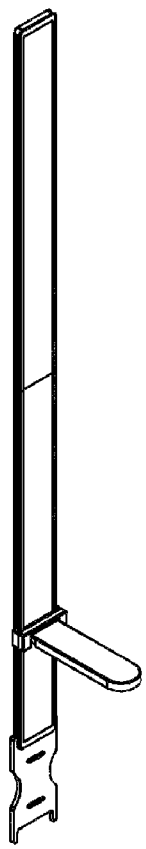
Figure 12:
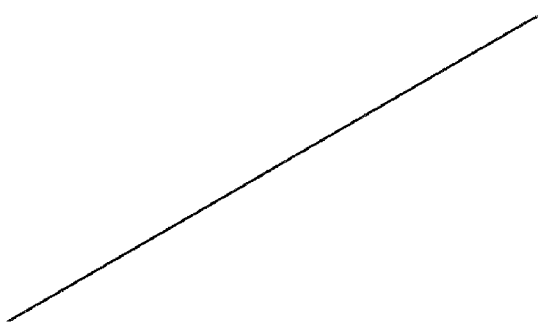

As shown in FIG. 10, after the scale 1 is fixed on the wall, it is possible to fold the measuring plate so that it is perpendicular to the scale 1, and thus height measurement of children is implemented (as shown in FIGS. 11 and 12).

After installation, a maximum measurement length and a minimum measurement height using the first method are less than those using the second method, and users can select any of the methods according to heights of children. In addition, since measurement range of the two methods are different, graduation of the scale 1 can use a sticker with graduation, and a method corresponds to a measurement range of the sticker, and only needs adhering the corresponding the sticker to the scale 1.

To summarize, the invention features simple structure, and easy transportation and installation, and takes up small indoor space during use, and measurement results are very accurate.

Industrial applicability of the invention is: since most conventional height measuring devices are integrated with devices, such as weight balances and so on, and no height measuring device featuring convenient installation and usage is used, the invention is disposed on the wall, takes less indoor space, features convenient transportation and accurate measurement results, and is suitable for mass industrial production.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A height measuring device, comprising
a scale, comprising graduation and a measuring part; and
a positioning plate; wherein
said graduation and said measuring part are disposed on a right side of said scale;
said measuring part is capable of moving along said graduation and indicating height;
a measuring plate is disposed on said measuring part, and capable of folding as being perpendicular to or parallel to said scale;
a top edge of said scale is capable of being buckled with a bottom edge of said positioning plate;
a bottom edge of said scale is capable of being buckled with a top edge of said positioning plate; and
a fixing part is disposed at the back of each of said scale and said positioning plate, and capable of being disposed in a vertical plane.

2. The height measuring device of claim 1, wherein a pair of buckling parts is disposed on a right side of said positioning plate, and the back of said scale, and capable of being buckled with each other.

3. The height measuring device of claim 1, wherein
said scale is divided into multiple sections; and
a folding mechanism is disposed between two adjacent sections whereby facilitating folding of said sections.

4. The height measuring device of claim 1, wherein
said scale is divided into multiple sections; and
said sections are connected to each other in a manner of inserting.

5. The height measuring device of claim 1, wherein a pair of arc-shaped concave parts is disposed on both sides of the center of said positioning plate.

6. The height measuring device of claim 1, wherein an upper part and a lower part of said positioning plate are axially symmetric to each other.

7. A height measuring device, comprising
a scale, comprising graduation and a measuring part; and
a positioning plate; wherein
said graduation and said measuring part are disposed on a right side of said scale;
said measuring part is capable of moving along said graduation and indicating height;

a measuring plate is disposed on said measuring part, and capable of folding as being perpendicular to or parallel to said scale;

a pair of buckling parts is disposed on a right side of said positioning plate, and the back of said scale, and capable of being buckled with each other;

a bottom edge of said scale is capable of being buckled with a top edge of said positioning plate; and a fixing part is disposed at the back of each of said scale and said positioning plate, and capable of being disposed in a vertical plane.

8. The height measuring device of claim 7, wherein said scale is divided into multiple sections; and
a folding mechanism is disposed between two adjacent sections whereby facilitating folding of said sections.

9. The height measuring device of claim 7, wherein said scale is divided into multiple sections; and
said sections are connected to each other in a manner of inserting.

10. The height measuring device of claim 7, wherein a pair of arc-shaped concave parts is disposed on both sides of the center of said positioning plate.

11. The height measuring device of claim 7, wherein an upper part and a lower part of said positioning plate are axially symmetric to each other.

* * * * *